(12) United States Patent
Weng et al.

(10) Patent No.: US 8,818,810 B2
(45) Date of Patent: Aug. 26, 2014

(54) SPEAKER VERIFICATION IN A HEALTH MONITORING SYSTEM

(75) Inventors: Fuliang Weng, Mountain View, CA (US); Taufiq Hasan, Dallas, TX (US); Zhe Feng, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 419 days.

(21) Appl. No.: 13/340,213

(22) Filed: Dec. 29, 2011

(65) Prior Publication Data
US 2013/0173268 A1    Jul. 4, 2013

(51) Int. Cl.
*G10L 15/00* (2013.01)
(52) U.S. Cl.
USPC .................. 704/246; 704/250; 379/88.02
(58) Field of Classification Search
USPC ................. 704/246, 250; 379/88.02
See application file for complete search history.

(56) References Cited

U.S. PATENT DOCUMENTS

| | | | |
|---|---|---|---|
| 4,653,097 A | | 3/1987 | Watanabe et al. |
| 5,127,043 A | | 6/1992 | Hunt et al. |
| 5,265,191 A | | 11/1993 | McNair |
| 5,297,194 A | * | 3/1994 | Hunt et al. ............... 379/88.02 |
| 5,365,574 A | | 11/1994 | Hunt et al. |
| 5,414,755 A | | 5/1995 | Bahler et al. |
| 5,517,558 A | * | 5/1996 | Schalk .................... 379/88.02 |
| 5,752,231 A | | 5/1998 | Gammel et al. |
| 5,774,841 A | | 6/1998 | Salazar et al. |
| 5,940,476 A | | 8/1999 | Morganstein et al. |
| 6,064,963 A | | 5/2000 | Gainsboro |
| 6,246,987 B1 | | 6/2001 | Fisher et al. |
| 6,292,782 B1 | | 9/2001 | Weideman |
| 6,456,698 B1 | | 9/2002 | Morganstein et al. |
| 6,477,500 B2 | | 11/2002 | Maes |
| 6,505,155 B1 | | 1/2003 | Vanbuskirk et al. |
| 6,523,009 B1 | | 2/2003 | Wilkins |
| 6,556,127 B1 | | 4/2003 | Moser et al. |
| 6,760,701 B2 | | 7/2004 | Sharma et al. |
| 6,853,716 B1 | | 2/2005 | Shaffer et al. |
| 7,240,007 B2 | | 7/2007 | Junqua et al. |
| 7,300,402 B2 | | 11/2007 | Iliff |
| 7,433,828 B2 | | 10/2008 | Brinkman et al. |
| 7,493,264 B1 | | 2/2009 | Kelly et al. |
| 7,529,677 B1 | | 5/2009 | Wittenberg |
| 7,590,538 B2 | * | 9/2009 | St. John ................... 704/246 |
| 7,668,733 B2 | | 2/2010 | Glimp et al. |
| 7,684,966 B1 | | 3/2010 | Genovese |

(Continued)

FOREIGN PATENT DOCUMENTS

WO    WO 2011/002735 A1    1/2011

OTHER PUBLICATIONS

International Search Report in corresponding PCT application (i.e., PCT/US2012/071633), mailed Mar. 28, 2013 (10 pages).

(Continued)

*Primary Examiner* — Daniel D Abebe
(74) *Attorney, Agent, or Firm* — Maginot, Moore & Beck

(57) ABSTRACT

A method for verifying that a person is registered to use a telemedical device includes identifying an unprompted trigger phrase in words spoken by a person and received by the telemedical device. The telemedical device prompts the person to state a name of a registered user and optionally prompts the person to state health tips for the person. The telemedical device verifies that the person is the registered user using utterance data generated from the unprompted trigger phrase, name of the registered user, and health tips.

21 Claims, 4 Drawing Sheets

(56) References Cited

U.S. PATENT DOCUMENTS

| | | |
|---|---|---|
| 7,766,223 B1 | 8/2010 | Mello et al. |
| 7,769,600 B2 | 8/2010 | Iliff |
| 7,835,913 B2 | 11/2010 | Aubauer |
| 7,962,340 B2 | 6/2011 | Comerford et al. |
| 7,992,196 B2 | 8/2011 | Gierach |
| 7,995,995 B2 | 8/2011 | Novack et al. |
| 8,050,917 B2 * | 11/2011 | Caspi et al. ............. 704/238 |
| 8,694,315 B1 * | 4/2014 | Sheets et al. ............. 704/246 |
| 2003/0125944 A1 * | 7/2003 | Wohlsen et al. ............. 704/246 |
| 2004/0250085 A1 | 12/2004 | Tattan et al. |
| 2005/0154588 A1 | 7/2005 | Janas, III et al. |
| 2007/0033041 A1 | 2/2007 | Norton |
| 2007/0038460 A1 | 2/2007 | Navratil et al. |
| 2007/0043570 A1 | 2/2007 | Scholl |
| 2007/0112571 A1 | 5/2007 | Thirugnana |
| 2007/0143307 A1 | 6/2007 | Bowers et al. |
| 2008/0104410 A1 | 5/2008 | Brown et al. |
| 2008/0147741 A1 | 6/2008 | Gonen et al. |
| 2008/0221888 A1 | 9/2008 | Greene et al. |
| 2008/0281600 A1 | 11/2008 | Kuppuswamy et al. |
| 2008/0300877 A1 | 12/2008 | Gilbert et al. |
| 2009/0043580 A1 | 2/2009 | Mozer et al. |
| 2009/0192800 A1 | 7/2009 | Brandt |
| 2009/0292531 A1 | 11/2009 | Ryan et al. |
| 2009/0300745 A1 | 12/2009 | Dispensa |
| 2009/0309698 A1 | 12/2009 | Headley et al. |
| 2010/0145709 A1 | 6/2010 | Kumar |
| 2011/0022389 A1 | 1/2011 | Kim et al. |
| 2011/0162067 A1 | 6/2011 | Shuart et al. |
| 2011/0213739 A1 | 9/2011 | Benitez et al. |

OTHER PUBLICATIONS

Gruneich, Armin, "Biometrics—hype and reality," Internet & New Economy, No. 28, Deutsche Bank Research, May 22, 2002 (12 pages).

* cited by examiner

SPEAKER VERIFICATION IN A HEALTH MONITORING SYSTEM

TECHNICAL FIELD

This application relates generally to the field of automated speech recognition, and more particularly to speech recognition systems and methods that verify a speaker.

BACKGROUND

The fields of telemedicine and home healthcare have experienced strong growth in recent years. In a telemedicine system, a patient is geographically removed from the presence of a doctor or other healthcare provider. For example, the patient could be at home instead of on site at a healthcare facility. Telemedical devices enable the healthcare provider to monitor the health status of a patient and potentially diagnose and treat some medical problems without the need for the patient to travel to the healthcare facility. The use of telemedical systems has the potential to reduce the cost of healthcare, and to improve the quality of healthcare through increased patient monitoring.

Various known telemedicine systems provide a device to a patient that enables the patient to transmit medical data to a doctor or healthcare provider. Some devices are configured to record biosignals, such as heart rate, blood pressure, and respiration rates, and transmit data of the recorded biosignals to a database for later review. Other telemedicine systems provide reminders to a patient to take medications at prescribed times or to perform exercises as part of a physical therapy regimen.

While telemedicine systems have numerous potential advantages, such systems can also present difficulties to patients who often use telemedical devices without the assistance of a healthcare professional. Providing an intuitive user interface increases the effectiveness of the telemedical device and also increases the likelihood that patients will use the telemedical devices assiduously. In some environments, telemedical devices also need to distinguish between different patients to provide appropriate treatment to each patient. For example, in a retirement community a large group of patients may use telemedical devices, or members of the same family may each use a telemedical device for different treatments. Some forms of telemedical device are handheld units that are portable and can be inadvertently exchanged between patients. Thus, improvements to telemedical devices to ease interactions between the patient and the device and to ensure that the telemedical device provides an appropriate treatment to each patient would be beneficial.

SUMMARY

In accordance with one embodiment a method for verifying an identity of a person has been developed. The method includes generating, with an audio input device, audio data corresponding to utterances spoken by a person, identifying first utterance data in the audio data with an audio data processor, generating an output with a user interface device to prompt the person to speak a registration name in response to the identified first utterance data corresponding to a predetermined trigger utterance, storing the identified first utterance data in a memory in response to the identified first utterance data corresponding to the predetermined trigger utterance, generating audio data corresponding to the spoken registration name with the audio input device, identifying second utterance data in the audio data corresponding to the spoken registration name with the audio data processor, storing the identified second utterance data in the memory, verifying, with a speaker verification module, that the person is a user registered in a registration database in association with the registration name in response to the first and second utterance data stored in the memory corresponding to a predetermined model of a voice of the user registered in the registration database in association with the registration name, and generating an output with the user interface device to offer services to the person in response to the speaker verification module verifying that the person is the user registered in the registration database.

In accordance with another embodiment, a telemedical device with speaker verification has been developed. The telemedical device includes an audio input device configured to generate audio data from utterances spoken by a person, an audio data processor operatively connected to the audio input device and configured to generate utterance data from audio data generated by the audio input device, a memory configured to store a plurality of utterance data generated by the audio data processor, a registration database configured to associate at least one user with a registration name and a voice model corresponding to the at least one user, a speaker verification module operatively connected to the memory and the registration database, a user interface device; and a controller operatively connected to the audio input device, audio data processor, memory, registration database, speaker verification module, and user interface device. The controller is configured to activate the audio input device to receive sounds including utterances spoken by a person and to generate audio data corresponding to the utterances without prompting the person to speak, identify first utterance data in audio data corresponding to the utterances spoken by the person with the audio data processor, store the identified first utterance data in the memory, generate an output with the user interface device to prompt the person to speak a registration name in response to the first utterance data corresponding to a predetermined trigger utterance, generate audio data corresponding to the spoken registration name with the audio input device, identify second utterance data in the audio data corresponding to the spoken registration name with the audio data processor, store the identified second utterance in the memory, verify, with a speaker verification module, that the person speaking the registration name is a user registered in a registration database in association with the registration name in response the first and second utterance data stored in the memory corresponding to a predetermined model of a voice of the user registered in the registration database in association with the registration name, and generate an output with the user interface device to offer services to the person in response to the speaker verification module verifying that the person speaking the registration name is the user.

DETAILED DESCRIPTION

Figure 1:
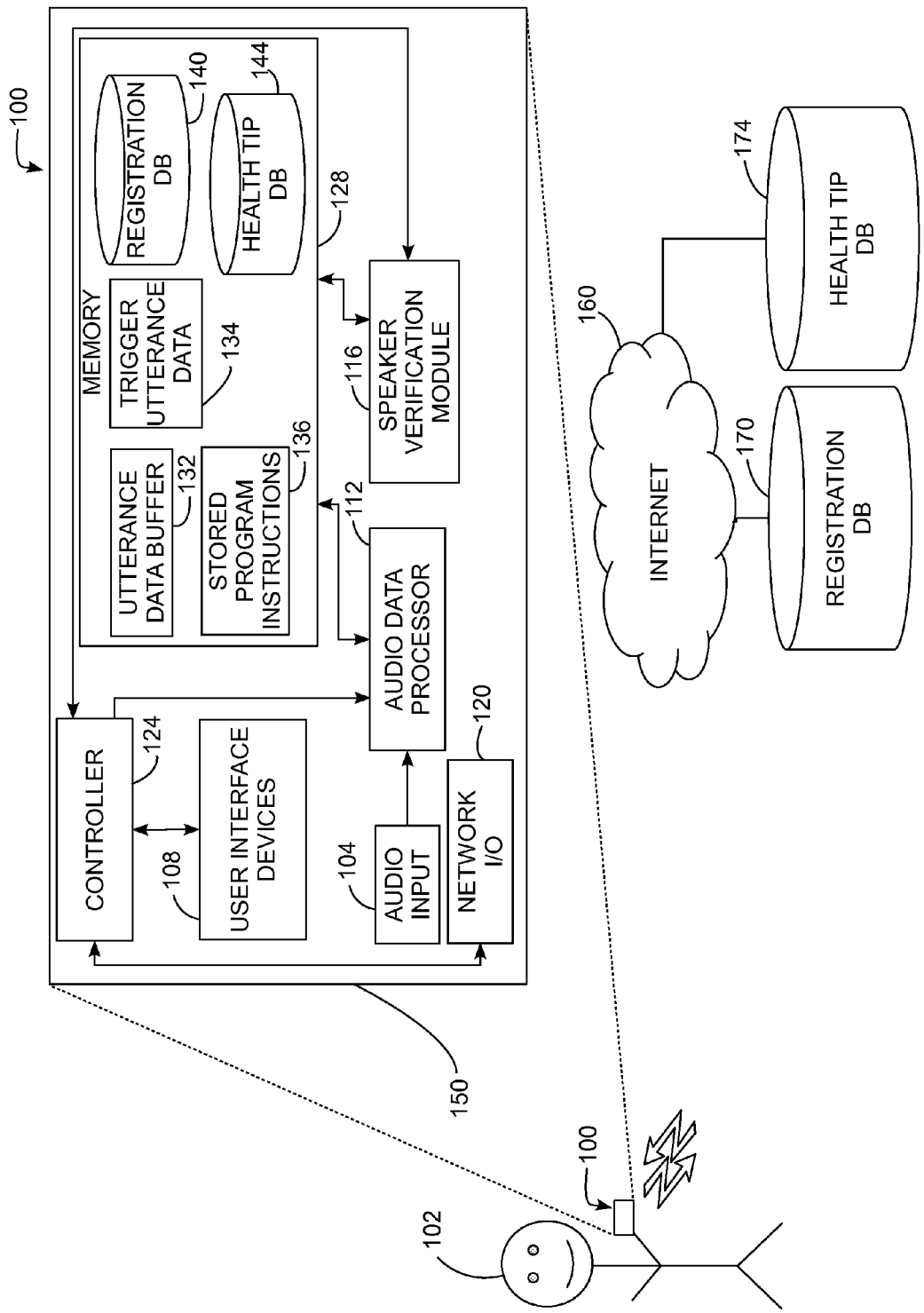
FIG. 1 is a schematic diagram of a handheld telemedical device used by a patient.

For a general understanding of the details for the systems and processes disclosed herein, the drawings are referenced throughout this document. In the drawings, like reference numerals designate like elements. As used herein, the term "utterance" refers to anything spoken by a human including words and phrases. The term "utterance data" refers to data corresponding to one or more utterances. The utterance data can correspond to a direct sound recording of the utterance, or be processed data generated from a speech recognizer, which typically includes a front-end processor, such as a digital signal processor, acoustic modeler, and a language model.

As used herein, the terms "verify" and "verification" refer to a process by which a telemedical device authenticates that a person who purports to be a registered user of the telemedical device is in fact the user. In a speaker verification process, the telemedical device verifies that a person is or is not a purported user by processing one or more utterances from the person. For example, if a telemedical device is configured to recognize the registered user "John Smith," then a person first enters input to the telemedical device indicating that he is the registered user John Smith and provides one or more utterances that the telemedical device uses to verify that the person is or is not the registered user John Smith using a predetermined voice model from the registered user John Smith.

As used herein, the term "health tip" refers to a word or phrase that pertains to advice or information about the health and well-being of a patient. For example, the phrase "I should walk one mile today" is a health tip about exercise that a patient should perform. Some health tips are generic to almost any patient, such as a nutritional health tip "I should eat fresh vegetables." Other health tips can be directed to a specific patient. For example, a health tip directed to a patient with a drug prescription is "I should take my drug prescription at the appropriate time." In the examples provided, the language in the health tips is constructed in the first-person from the perspective of the patient. As described below, a patient speaks one or more health tips out loud as part of a verification process for using a telemedical device. Some health tips are provided in the first person perspective to reinforce the applicability of the health tip to the patient, although other health tips include phrases and words in a variety of forms.

FIG. 1 depicts a telemedical device 100. The telemedical device 100 includes an audio input device 104, one or more user interface devices 108, audio data processor 112, speaker verification module 116, network input/output (I/O) device 120, controller 124 and memory 128. The memory 128 stores data for a buffer of recorded utterance data 132, stored program instructions 136, a registration database 140, and a health tip database 144. In one operating mode, the memory 128 also stores predetermined trigger utterance data 134. The memory 128 includes one or more devices such as random access memory (RAM), and non-volatile data storage devices such as magnetic media and solid-state data storage devices to store digital data. In the example of FIG. 1, the telemedical device 100 is contained within a housing 150 that is formed with a size and shape for handheld use by a person 102. The telemedical device 100 is configured to accept utterances from the person 102 to both verify that the person 102 is a registered user of the telemedical device 100 and to accept utterances from the person 102 to operate the telemedical device.

The telemedical device 100 includes one or more user interface devices 108 that are positioned within the housing 150. The user interface devices provide output information to the user and receive input information, commands, and utterances from the user. Common examples of output devices include visual display screens such as liquid crystal displays (LCDs) and other visual display screens, speakers that emit sounds and synthesized speech, haptic feedback devices, and the like. Common examples of input devices include microphones, which are also used as the audio input 104, keypads, touchscreen interfaces that are integrated with a display screen, and tactile controls including buttons and switches. In particular, the user interface devices 108 enable the telemedical device to prompt the person 102 to provide utterances that are detected by the audio input 104.

The telemedical device 100 includes a network I/O device 120. Common examples of the network I/O device include wireless data communication modules such as wireless local area network (WLAN), wireless wide area network (WWAN) network devices. Other I/O devices included wired network devices, such as Ethernet devices, or a serial device, such as a USB device, to connect the telemedical device 100 to a separate computer that provides access to data networks. The network I/O devices enable the telemedical device 100 to communicate with online databases and healthcare providers via a data network such as the Internet.

The audio input 104 typically includes one or more microphones that are positioned in the housing 150 at locations that enable detection of sounds in the environment around the telemedical device 100. The audio input device 104 functions to detect utterances spoken by the person 102 and generates audio data from the utterances. In some embodiments the audio data includes analog electrical signals generated by one or more microphones. In other embodiments the audio input 104 includes an analog to digital converter that converts an analog signal corresponding to the received utterances into a digital signal, such as a pulse-code modulated (PCM) signal or other digital signal, which represents the recorded sounds. Some embodiments of the audio input device 104 include signal filters, echo cancellation circuits, and other signal processing devices that improve the quality of the audio data.

The audio data processor 112 receives audio data from the audio input device 104 and generates utterance data from the audio data. The audio data processor 112 includes an acoustic modeler and a language model that process the audio data to extract spoken words and phrases from the audio data. The audio data processor 112 is operatively connected to the memory 128. In one operating mode, the audio data processor 112 compares the generated utterance data to predetermined utterance data 134 in the memory 128 that corresponds to one or more trigger phrases. If the generated utterance data correspond to the utterance data of the predetermined trigger phrase, the controller 124 activates other components in the telemedical device 100, including a speaker verification module. In another operating mode, the audio data processor 112 compares the generated utterance data to utterance data corresponding to one or more health tips in the health tip database 144. When the audio data processor 112 generates utterance data corresponding to predetermined utterance data of various types, the audio data processor 112 stores the utterance data in the utterance data buffer 132 in the memory 128. The utterance data buffer 132 accumulates multiple sets of utterance data that are used to verify that the person 102 is a registered user for the telemedical device 100.

The speaker verification module 116 is operatively connected to the memory 128 and controller 124. The speaker verification module 116 reads utterance data from the utterance data buffer 132 and verifies that the utterance data corresponds to a speech model stored in the registration database 140 in association with the purported registered name of the person using the telemedical device 100. The utterance data buffer 132 stores accumulated utterance data generated by the audio data processor 112 including utterance data corresponding to a trigger phrase, the registered user name, and one or more spoken health tips. In one embodiment, the speaker verification module 116 generates a confidence score that corresponds to the likelihood that the utterance data in the utterance data buffer 132 corresponds to the voice model of the registered user. The speaker verification module 116 also generates a confidence score corresponding to an impostor voice model, which corresponds to various voice characteristics of one or more voices belonging to people other than the registered user. The impostor voice model is trained beforehand on a large amount of data from different people using a Gaussian mixture model (GMM) or other techniques depending on the speaker verification method used in module 116. The telemedical device 100 stores the generated impostor voice model in the registration database 140 for use during a speaker verification process.

If the confidence score for the voice model of the user is higher than for the impostor by at least a predetermined threshold, then the speaker verification module 116 verifies that the utterance data corresponds to the voice model of the registered user. If the confidence score for the voice model of the impostor is higher than for the registered user by at least a predetermined threshold, then the speaker verification module 116 verifies that the utterance data does not correspond to the voice model of the registered user. In some cases, insufficient utterance data are available to generate confidence scores that clearly indicate whether the utterance data do or do not correspond to the voice model of the user. The telemedical device 100 prompts the person 102 to speak one or more health tips to generate additional utterance data that is added to the utterance data buffer 132, and the additional utterance data in the data buffer 132 increases the likelihood that the speaker verification module 116 has sufficient utterance data to verify the person 102 with the voice model of the registered user.

Figure 3:
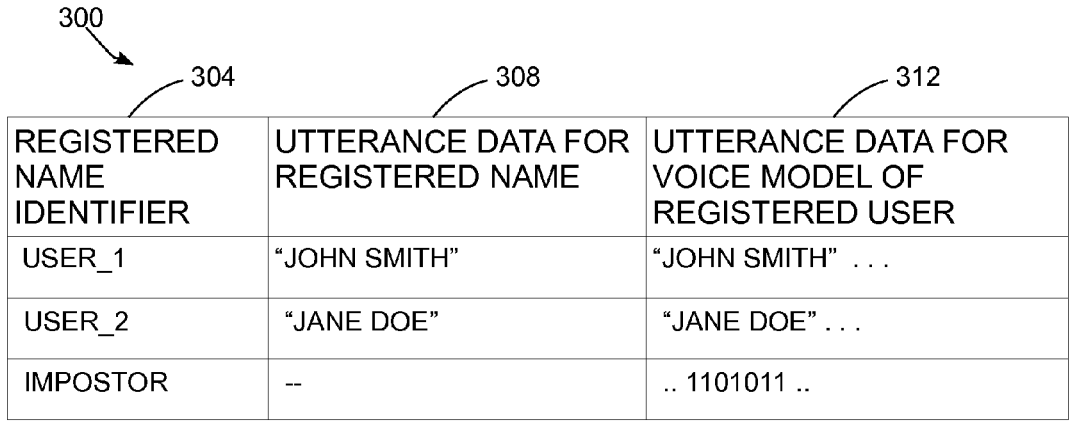
FIG. 3 is an example of a registration database used with a telemedical device.

The registration database 140 includes registration data corresponding to one or more users who are authorized to use the telemedical device 100. FIG. 3 depicts an example of data stored in a registration database 300. The registration database 300 includes columns corresponding to a registered name identifier 304, utterance data corresponding to the registered name 308, and utterance data for a voice model that corresponds to the registered user 312. The registered name identifier 304 is a string or numeric identifier that identifies each user of the telemedical device 100. In the example of FIG. 3, the "IMPOSTOR" name is a special entry in the registration database that stores utterance data corresponding to one or more voice models that are not one of the registered users.

In the table 300, the utterance data for the registered name of each user 308 and the utterance data for the voice model of each user 312 both include utterance data obtained from utterances spoken by a user during an enrollment process. In the enrollment process the user speaks utterances comprised of one or more series of words and phrases including the registration name and a series of training phrases. The voice model of the registered user is generated using utterance data generated from the utterances comprised of the registration name and training phrases. The enrollment process is typically performed one time prior to a patient receiving the telemedical device. The telemedical device 100 can perform an enrollment process directly, or a separate enrollment system performs the registration and the telemedical device 100 receives the user information and generated voice model. For example, the telemedical device 100 may download registration data for one or more enrolled users from an online registration database 170 that is accessed through the Internet 160 via the network I/O device 120.

The utterance data for the registered name 308 stores utterance data corresponding to a registered name of a user who is registered to use the telemedical device 100. The registered name can simply be the name of a user, e.g. "John Smith" or could be a special login name or numeric patient number. The registered names are listed in FIG. 3 as text for illustrative purposes, but are typically stored as binary utterance data in the registration database 300. The utterance data for the voice model 312 includes utterance data corresponding to multiple utterances provided by the registered user. In some embodiments the utterance data used to generate the voice model is provided one time during the enrollment process. In other embodiments, the utterance data 312 are updated with newly generated utterance data after the telemedical device 100 verifies that a particular registered user is speaking. The updated utterance data account for gradual changes in the voice of a user that occur during treatment with the telemedical device 100. The utterance data for the voice models are typically stored in a binary data format in the registration database 140.

Figure 4:
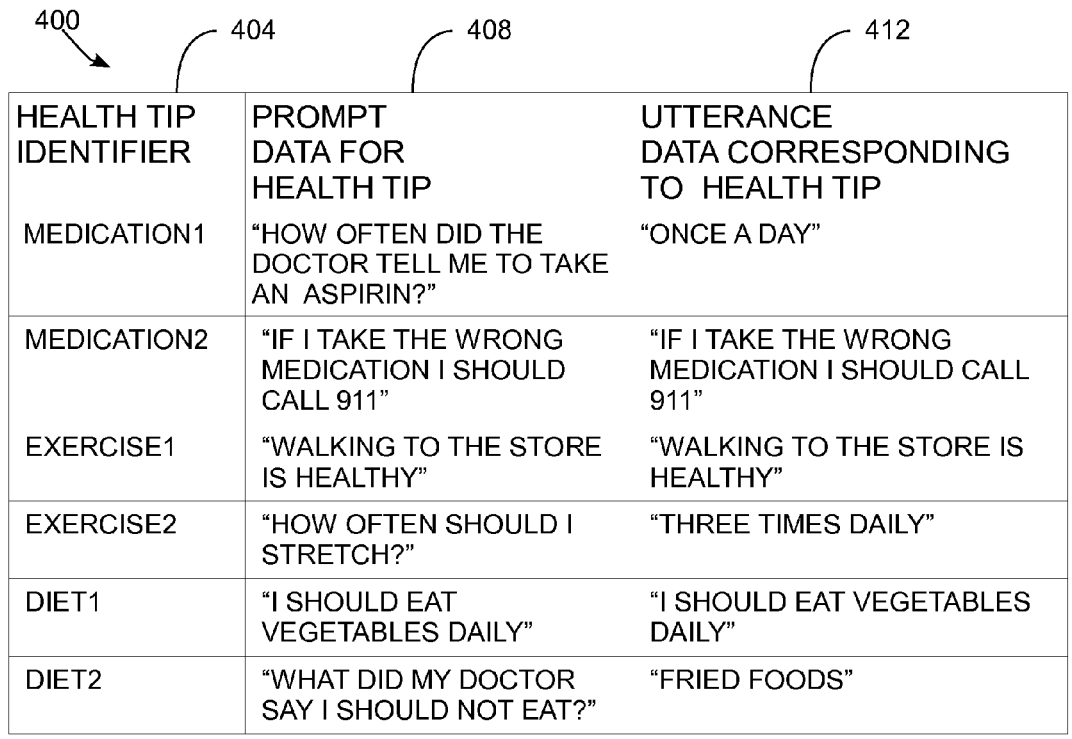
FIG. 4 is an example of a health tip database used with a telemedical device.

The health tip database 144 includes a data associated with a plurality of health tips. FIG. 4 depicts an example of data stored in a health tip database. A table 400 includes columns corresponding to a health tip identifier 404, data used to prompt the person to speak a health tip 408, and utterance data corresponding to the spoken health tip 412. Each row in the table 400 represents data corresponding to a single health tip, and the table 400 typically includes a plurality of health tips. The health tip identifier is a string or numeric value that identifies a particular health tip. In some embodiments, the telemedical device 100 associates selected health tips with particular patients using the health tip identifier 404 and registered name identifier 304 from the table 300 in FIG. 3.

The prompt data for the health tip 408 includes formatted data that enable the telemedical device 100 to generate a message to the user that prompts the user to speak a corresponding health tip. While the prompt data depicted in FIG. 4 are in the form of text, the prompt data can be stored in a variety of formats including audio data that the telemedical device outputs via a speaker and in the form of visual prompts displayed on a screen in the user interface devices 108. Some prompts provide a phrase for the user to repeat back to the telemedical device 100. Other health tip prompts provide a simple question to the user and the user speaks an answer to the question. In a question and answer configuration, the telemedical device 100 may display the answer on a display screen to assist the speaker in remembering the answer to the question.

The utterance data 412 correspond to a particular health tip. The utterance data are depicted as text in FIG. 4 for illustrative purposes, but utterance data are typically stored in a binary data format in the health tip database 144. In some embodiments, the utterance data 412 for each health tip correspond directly to recorded utterances of a registered user who speaks each health tip during an enrollment process prior to using the telemedical device. In other embodiments, the utterance data do not directly correspond to the voice of the registered user, but are instead generic to one or more voices. The audio data processor 112 is configured to compare utterance data generated from the audio data of an utterance to the predetermined utterance data 412 to identify whether the person 102 spoke the prompted health tip or spoke a different phrase.

In some embodiments, the telemedical device 100 retrieves stored in the health tip database 144 are retrieved from a separate health tip database 174 through the Internet 160 via the network I/O device 120. Healthcare providers populate the health tip database 174 with various health tips including generic health tips that are applicable to many patients, and specific health tips that are associated with particular registered users. The telemedical device 100 updates the health tips in the health tip database 144 periodically so that users receive a wide variety of health tips.

Referring again to FIG. 1, the controller 124 coordinates operation of the telemedical device 100, and, more particularly, controls the telemedical device to verify that a person interacting with the telemedical device is a registered user. Some embodiments of the telemedical device include a single microelectronic device, such as a processor, microcontroller, field programmable gate array (FPGA), application specific integrated circuit (ASIC), or other digital computing device, to implement the functionality of some or all of the controller 124, audio data processor 112, speaker verification module 116, and network I/O 120. The controller 124 executes software instructions held in the stored program instructions area 136 of the memory 128. In some embodiments, various components in the telemedical device 100 including the audio data processor 112 and speaker verification module 116 are implemented as software programs that are executed by the controller 116. Stored instructions to implement the functions of the audio data processor 112 and speaker verification module 116 are stored in the stored program area 136 of the memory 100. In other embodiments, one or both of the audio data processor 112 and speaker verification module 116 include specialized processing devices such as digital signal processors (DSPs). Still other embodiments perform the functions of the audio data processor 112 and speaker verification module 116 using a combination of hardware and software components. Various microelectronic components in the telemedical device can be combined into a single physical device in a "system on a chip" (SoC) configuration.

Figure 2:
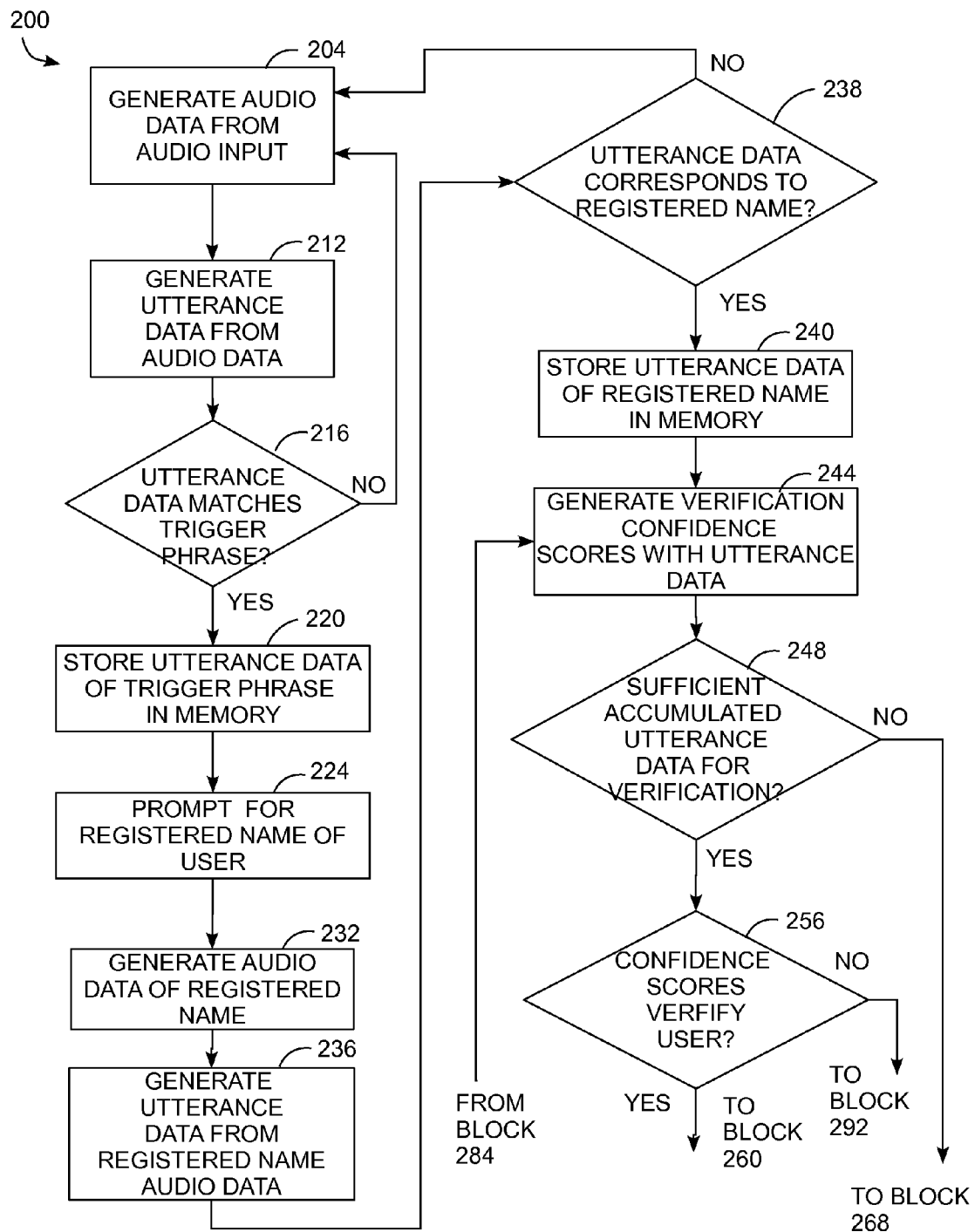
FIG. 2 is a block diagram of a process for verifying that a person is a registered user of a telemedical device.
Figure 2:
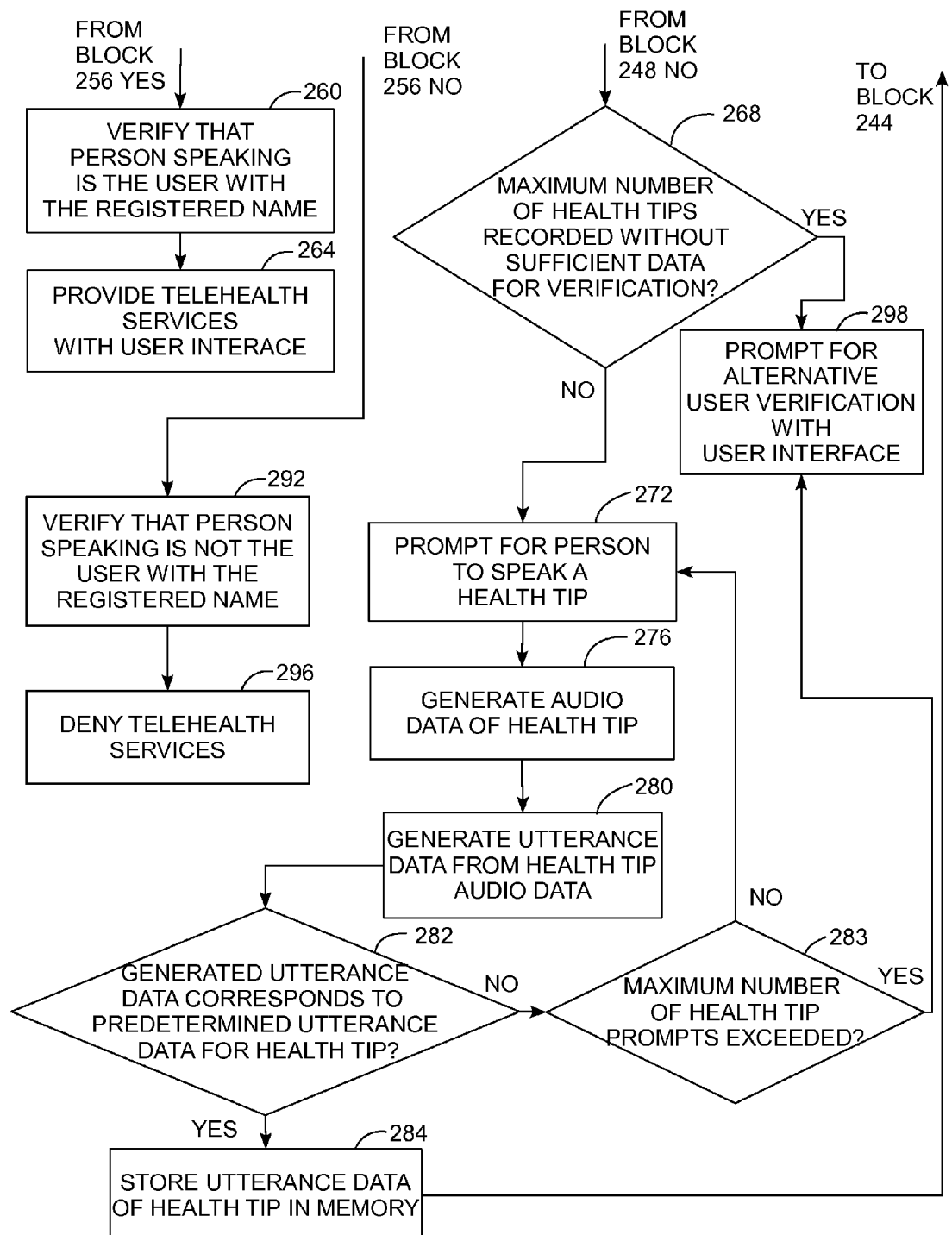

FIG. 2 depicts a process 200 for verification that the identity of a person purporting to be a registered user of a telemedical device matches the registered user through a speaker verification process. Process 200 is described in conjunction with the telemedical device 100 for illustrative purposes. As described below, the process being described as implementing a function or performing some action refers to a controller executing programmed instructions stored in a memory to operate one or more electronic components to implement the function or perform the action. Process 200 begins with the audio input device generating audio data from sounds received through an audio input device (block 204). In the telemedical device 100, the audio input device 104 includes one or more microphones receive sounds from the environment and the audio input device generates audio data from the received sounds. Process 200 generates utterance data from the audio signals (block 212), if the audio signals include utterances, and compares the utterance data to a predetermined trigger phrase (block 216). The trigger phrase is typically a word or multiple words that are not used in ordinary conversation to prevent inadvertent activation of the telemedical device 100. The telemedical device does not generate a prompt or request for a person to speak the trigger phrase.

The telemedical device 100 performs the process in blocks 204-216 continuously in a monitoring operating mode unit the person 102 speaks the trigger phrase. In the monitoring mode, various components in the telemedical device are deactivated or placed into low power operating modes that reduce the power consumption of the telemedical device 100. In embodiments of the telemedical device that operate via a battery, the low power mode prolongs the battery life of the telemedical device. The telemedical device 100 continues with process 200 when the audio data processor 112 generates utterance data from the audio signal that corresponds to the trigger utterance data 134.

In process 200, the utterance data corresponding to the trigger phrase are stored in a memory for later use in verifying the identity of the speaker (block 220). In the telemedical device 100, the utterance data are stored in the utterance data buffer 132. After receiving the trigger phrase, process 200 generates a prompt for the speaker to state the registration name of a registered user (block 224). The telemedical device 100 can generate an audible prompt using a speaker or visually display a request for the person 102 to speak the user name.

The telemedical device generates audio data corresponding to the spoken registered name (block 232), and generates utterance data corresponding to the audio data of the registered name (block 236). In the telemedical device 100, if the person 102 does not provide a registered name corresponding to one user in the registration database 140 (block 238), then the telemedical device 100 either prompts the speaker to repeat the name of the registered user or returns to the processing described in block 204 to monitor for the trigger phrase. After receiving utterance data corresponding to the name of a registered user (block 238), process 200 stores the utterance data corresponding to the name of the registered user in the memory (block 240). In the telemedical device 100, the utterance data corresponding to the registered name is stored in the utterance data buffer 132 in addition the utterance data from the trigger phrase.

Process 200 continues to generate one or more confidence scores for verification of the utterance data stored in the memory with the predetermined voice model of the user corresponding to the registered name (block 244). The speaker verification module 116 in the telemedical device 100 extracts the recorded utterance data from the utterance data buffer 132 and the utterance data corresponding to the voice model of the registered user from the registration database 140. In some embodiments, the registration database 140 stores speech models for more than one user, and process 200 selects the user corresponding to the spoken registration name to distinguish between different users who are registered to use the telemedical device 100. The speaker verification module 116 also extracts the utterance data from the impostor in the registration database 140.

In some instances, the utterance data for the trigger phrase and the registration name are sufficient for the speaker verification module 116 to generate confidence scores that clearly indicate if the person 102 is the user with the registered name (block 248). Process 200 measures the reliability of the confidence score identified in the processing of block 244 utilizing the amount of data accumulated. If the speaker verification module 116 verifies that the confidence score for the registered user voice model is higher than the confidence score for the impostor model by greater than a predetermined threshold (block 256) then the telemedical device 100 verifies that the person 102 is the user with the registered name (block 260) and the telemedical device 100 provides services to the user (block 264).

If the speaker verification module 116 identifies confidence scores that indicate the utterance data correspond to an impostor (block 256), then the speaker verification module 116 identifies that person 102 is not the registered user (block 292) and the telemedical device 100 denies telehealth services to the impostor (block 296). In some configurations, the telemedical device 100 maintains a count of failed verification attempts and the telemedical device blocks any additional attempts to verify a user with the telemedical device if the count exceeds a predetermined threshold. For example, if three consecutive attempts to verify a person with the telemedical device each result in the person being identified as an impostor, then the telemedical device locks out any users until a healthcare professional resets the device.

In some cases, the speaker verification module 116 generates confidence scores that are insufficient to verify that the person 102 is or is not the registered user (block 248). For example, if the confidence score generated for both the voice model of the registered user and the impostor voice model are below a predetermined threshold or if both confidence scores are within a predetermined range of each other, then the speaker verification module 116 may require additional utterance data to perform the verification. In another example, a high or low confidence score generated from an insufficient amount of utterance data has a low reliability. Process 200 collects additional utterance data to generate a confidence score with a sufficient degree of reliability to verify the speaker.

To generate additional utterance data, process 200 prompts for the person 102 to speak a health tip (block 272). The telemedical device selects a health tip from the health tip database 144 and generates an audio or visual prompt for the person 102. The audio input 104 generates audio data corresponding to the spoken health tip (block 276) and the audio data processor 112 generates utterance data from the audio data (block 280). The audio data processor 112 compares the generated utterance data to the predetermined utterance data for the selected health tip that is stored in the health tip database 144.

If the generated utterance data does not correspond to the health tip (block 282), then the telemedical device 100 repeats the prompt for the person to speak the health tip (block 272). The telemedical device 100 maintains a counter of the number of times that the generated utterance data does not correspond to the prompted health tip during process 200. If this count exceeds a predetermined maximum number (block 283), then the device 100 prompts for alternate verification with user interface (block 298). For example, if the user cannot provide the correct response for a health-tip for three consecutive times, the device 100 asks for alternate verification. If the generated utterance data corresponds to the health tip (block 282), then the generated utterance data are stored in the utterance data buffer 132 (block 284). Process 200 then returns to block 244 to perform speaker verification using all of the accumulated utterance data including the utterance data from the health tip.

In some cases, process 200 prompts for multiple health tips before sufficient utterance data are collected to verify if the person 102 is the registered user. The telemedical device 100 prompts for a different health tip during each iteration to provide a wider variety of utterance data to the speaker verification module 116. Process 200 implements a limit to the number of health tips that are accepted during the user verification process (block 268). For example, if process 200 receives the utterance data corresponding to five health tips but still lacks sufficient utterance data to verify if the person 102 is the registered user, then the speaker verification process 200 ends and the telemedical device 100 uses an alternative verification process (block 298). In one alternative verification process, the telemedical device generates a login prompt on a display screen in the user interface 108 and the person 102 enters a username and password via a keypad.

The telemedical device 100 and verification process 200 provide patients with a simple and effective verification procedure. Since the telemedical device 100 uses all of the valid utterance data received from the person, including the initial trigger phrase, to verify that the person is the registered user, the telemedical device 100 enables efficient verification of users with a minimal number of speech samples. Additionally, the health tip speech samples provide patients with health advice during the verification process to increase the medical benefit provided to each patient even during the initial verification process.

While the invention has been illustrated and described in detail in the drawings and foregoing description, the same should be considered as illustrative and not restrictive in character. For example, while the examples of speech described herein are in the English language, the telemedical device 100 can be configured to recognize speech and generate utterance data from a wide range of languages. It is understood that only the preferred embodiments have been presented and that all changes, modifications and further applications that come within the spirit of the invention are desired to be protected.

We claim:

1. A method for verifying an identity of a person:
generating, with an audio input device, audio data corresponding to utterances spoken by a person;
identifying first utterance data in the audio data with an audio data processor;
generating an output with a user interface device to prompt the person to speak a registration name in response to the identified first utterance data corresponding to a predetermined trigger utterance;
storing the identified first utterance data in a memory in response to the identified first utterance data corresponding to the predetermined trigger utterance;
generating audio data corresponding to the spoken registration name with the audio input device;
identifying second utterance data in the audio data corresponding to the spoken registration name with the audio data processor;
storing the identified second utterance data in the memory;
verifying, with a speaker verification module, that the person is a user registered in a registration database in association with the registration name in response to the first and second utterance data stored in the memory corresponding to a predetermined model of a voice of the user registered in the registration database in association with the registration name; and
generating an output with the user interface device to offer services to the person in response to the speaker verification module verifying that the person is the user registered in the registration database.

2. The method of claim 1 further comprising:
generating an output with the user interface device to prompt the person to speak a predetermined phrase in response to the speaker verification module identifying that the first utterance data and second utterance data in the memory are insufficient to verify the person with the predetermined model of the voice of the user;
generating audio data corresponding to the spoken predetermined phrase with the audio input device;
identifying third utterance data in the audio data corresponding to the spoken predetermined phrase with the audio data processor;
storing the third utterance data in the memory; and
verifying, with the speaker verification module, that the person is the user registered in the registration database in response the first, second, and third utterance data stored in the memory corresponding to a predetermined model of a voice of the user registered in the registration database.

3. The method of claim 2 further comprising:
storing the third utterance data in the memory in response to the third utterance data corresponding to predetermined utterance data of the predetermined phrase.

4. The method of claim 2 further comprising:
generating the output with the user interface device to prompt the person to speak the predetermined phrase a second time in response to the third utterance data not corresponding to predetermined utterance data of the predetermined phrase.

5. The method of claim 2, the user interface device generating a prompt for the person to speak a health tip as the predetermined phrase.

6. The method of claim 5, the user interface device generating a prompt for the person to speak a health tip that is associated with the registration name in the registration database.

7. The method of claim 2 further comprising:
verifying, with the speaker verification module, that the person speaking the registration name is not the user registered in the registration database in association with the registration name in response to the first, second, and third utterance data stored in the memory not corresponding to the predetermined model of the voice of the user registered in the registration database; and
generating an output with the user interface device to deny services to the person in response to the speaker verification module verifying that the person speaking the registration name is not the user registered in the registration database.

8. The method of claim 2 further comprising:
continuing to generate an output with the user interface device to prompt the person to speak at least one additional predetermined phrase in response to the speaker verification module identifying that the first, second, and third utterance data in the memory are insufficient to verify the person with the predetermined model of the voice of the user;
generating audio data corresponding to the at least one additional predetermined phrase spoken by the person with the audio input device;
identifying at least one additional utterance data in the audio data corresponding to the at least one additional predetermined phrase with the audio data processor;
storing the at least one additional utterance data in the memory; and
verifying, with the speaker verification module, that the person is the user registered in the registration database in association with the registration name in response the first, second, third, and at least one additional utterance data stored in the memory corresponding to the predetermined model of the voice of the user registered in the registration database.

9. The method of claim 8 further comprising:
identifying that the speaker verification module is unable to verify that the person is the user associated with the registration name in the registration database in response to the memory having insufficient utterance data for the speaker verification module to verify that the person is the user after a number of additional utterance data exceeding a predetermined threshold are stored in the memory.

10. The method of claim 9 further comprising:
prompting the person, with the user interface device, to input information for verification of the person with a user input device that is different from the audio input device in response to the speaker verification module being unable to verify that the person is the user associated with the registration name in the registration database.

11. A telemedical device with speaker verification comprising:
an audio input device configured to generate audio data from utterances spoken by a person;
an audio data processor operatively connected to the audio input device and configured to generate utterance data from audio data generated by the audio input device;
a memory configured to store a plurality of utterance data generated by the audio data processor;
a registration database configured to associate at least one user with a registration name and a voice model corresponding to the at least one user;
a speaker verification module operatively connected to the memory and the registration database;
a user interface device; and
a controller operatively connected to the audio input device, audio data processor, memory, registration database, speaker verification module, and user interface device, the controller being configured to:
activate the audio input device to receive sounds including utterances spoken by a person and to generate audio data corresponding to the utterances without prompting the person to speak;
identify first utterance data in audio data corresponding to the utterances spoken by the person with the audio data processor;
store the identified first utterance data in the memory;
generate an output with the user interface device to prompt the person to speak a registration name in response to the first utterance data corresponding to a predetermined trigger utterance;
generate audio data corresponding to the spoken registration name with the audio input device;
identify second utterance data in the audio data corresponding to the spoken registration name with the audio data processor;
store the identified second utterance in the memory;
verify, with a speaker verification module, that the person speaking the registration name is a user registered in a registration database in association with the registration name in response the first and second utterance data stored in the memory corresponding to a predetermined model of a voice of the user registered in the registration database in association with the registration name; and
generate an output with the user interface device to offer services to the person in response to the speaker verification module verifying that the person speaking the registration name is the user.

12. The telemedical device of claim 11, the controller being further configured to:
generate an output with the user interface device to prompt the person to speak a predetermined phrase in response to the speaker verification module identifying that the first and second utterance data in the memory are insufficient to verify the person with the predetermined model of the voice of the user;
generate audio data corresponding to the spoken predetermined phrase with the audio input device;
identify third utterance data in the audio data corresponding to the spoken predetermined phrase with the audio data processor;
store the third utterance data in the memory; and verify, with the speaker verification module, that the person speaking the registration name is the user registered in the registration database in response to the first, second, and third utterance data stored in the memory corresponding to a predetermined model of a voice of the user registered in the registration database.

13. The telemedical device of claim 12, the audio data processor being further configured to:
store the third utterance data in the memory in response to the third utterance data corresponding to predetermined utterance data of the predetermined phrase.

14. The telemedical device of claim 12, the controller being further configured to:
generate the output with the user interface device to prompt the person to speak the predetermined phrase a second time in response to the third utterance data not corresponding to predetermined utterance data of the predetermined phrase.

15. The telemedical device of claim 12, the user interface device being further configured to:
generate a prompt for the person to speak a health tip as the predetermined phrase.

16. The telemedical device of claim 15, the user interface device being further configured to:
generate a prompt for the person to speak a health tip that is associated with the registration name in the registration database.

17. The telemedical device of claim 12, the controller being further configured to:
verify, with the speaker verification module, that the person speaking the registration name is not the user registered in the registration database in association with the registration name in response to the first, second, and third utterance data stored in the memory not corresponding to the predetermined model of the voice of the user registered in the registration database; and
generate an output with the user interface device to deny services to the person in response to the speaker verification module verifying that the person speaking the registration name is not the user registered in the registration database.

18. The telemedical device of claim 12, the controller being further configured to:
continue to generate an output with the user interface device to prompt the person to speak at least one additional predetermined phrase in response to the speaker verification module identifying that the first, second, and third utterance data stored in the memory are insufficient to verify the first, second, and third utterance data stored in the memory correspond with the predetermined model of the voice of the user registered in the registration database;
generate audio data corresponding to the at least one additional predetermined phrase spoken by the person with the audio input device;
identify at least one additional utterance data in the audio data corresponding to the at least one additional predetermined phrase with the audio data processor;
store the at least one additional utterance data in the memory; and
verify, with the speaker verification module, that the person is the user registered in the registration database in association with the registration name in response the first, second, third, and at least one additional utterance data stored in the memory corresponding to the predetermined model of the voice of the user registered in the registration database.

19. The telemedical device of claim 18, the controller being further configured to:
identify that the speaker verification module is unable to verify that the person is the user associated with the registration name in the registration database in response to the memory having insufficient utterance data for the speaker verification module to verify that the person is the user after a number of additional utterance data exceeding a predetermined threshold are stored in the memory.

20. The telemedical device of claim 19, the controller being further configured to:
prompt the person, with the user interface device, to input information for verification of the person with a user input device that is different from the audio input device in response to the speaker verification module verifying that the person is not the user associated with the registration name in the registration database.

21. The telemedical device of claim 11 further comprising:
a handheld housing in which the audio input device, audio data processor, memory, registration database, speaker verification module, user interface device, and controller are positioned.

* * * * *